United States Patent [19]

Curro et al.

[11] Patent Number: 5,366,782
[45] Date of Patent: Nov. 22, 1994

[54] POLYMERIC WEB HAVING DEFORMED SECTIONS WHICH PROVIDE A SUBSTANTIALLY INCREASED ELASTICITY TO THE WEB

[75] Inventors: John J. Curro; Michele A. Maden, both of Cincinnati, Ohio

[73] Assignee: The Procter & Gamble Company, Cincinnati, Ohio

[21] Appl. No.: 936,195

[22] Filed: Aug. 25, 1992

[51] Int. Cl.⁵ ............................................. B32B 3/10
[52] U.S. Cl. ...................................... 428/137; 428/131; 428/224; 428/284; 604/358; 604/378
[58] Field of Search ............... 428/131, 224, 137, 284; 604/358, 378

[56] References Cited

U.S. PATENT DOCUMENTS

| | | | |
|---|---|---|---|
| 2,031,703 | 2/1936 | Galligan et al. | 154/55 |
| 2,075,189 | 3/1937 | Galligan et al. | 154/33 |
| 2,158,087 | 5/1939 | Rowe et al. | 154/30 |
| 2,158,929 | 5/1939 | Dunajeff | 29/180 |
| 2,240,274 | 4/1941 | Wade | 154/1 |
| 2,582,294 | 1/1952 | Stober | 18/55 |
| 2,946,087 | 7/1960 | Haroldson et al. | 18/2 |
| 2,960,145 | 11/1960 | Ruegenberg | 154/30 |
| 2,995,481 | 8/1961 | Muller | 154/55 |
| 3,048,895 | 8/1962 | Bottomley | 18/57 |
| 3,104,937 | 9/1963 | Wyckoff et al. | 18/48 |
| 3,131,425 | 5/1964 | Jacobs et al. | 18/4 |
| 3,137,746 | 6/1964 | Seymour et al. | 264/73 |
| 3,150,576 | 9/1964 | Gewiss | 93/84 |
| 3,161,557 | 12/1964 | Muller | 156/462 |
| 3,179,024 | 4/1965 | Muller | 93/1 |
| 3,208,100 | 9/1965 | Nash | 18/1 |
| 3,211,816 | 10/1965 | Brown, Jr. | 264/95 |
| 3,220,056 | 11/1965 | Walton | 18/19 |
| 3,226,280 | 12/1965 | Muller | 156/510 |
| 3,233,029 | 2/1966 | Rasmussen | 264/288 |
| 3,283,378 | 11/1966 | Cramton | 24/16 |
| 3,354,253 | 11/1967 | Rasmussen | 264/288 |
| 3,390,218 | 6/1968 | Painter et al. | 264/282 |
| 3,416,772 | 12/1968 | Sheehan | 225/3 |
| 3,462,053 | 8/1969 | Behr | 226/6 |
| 3,470,053 | 9/1969 | Rule | 156/207 |
| 3,488,415 | 1/1970 | Patchell et al. | 264/154 |
| 3,496,259 | 2/1970 | Guenther | 264/156 |
| 3,507,943 | 4/1970 | Such et al. | 264/103 |
| 3,511,742 | 5/1970 | Rasmussen | 161/109 |
| 3,517,098 | 6/1970 | Rasmussen | 264/288 |
| 3,550,826 | 12/1970 | Salmela | 225/3 |
| 3,574,809 | 4/1971 | Fairbanks et al. | 264/167 |
| 3,577,586 | 5/1971 | Kalwaites et al. | 18/1 |
| 3,616,157 | 10/1971 | Smith | 161/124 |
| 3,624,874 | 12/1971 | Lauchenauer | 26/63 |
| 3,666,517 | 5/1972 | Isaacson | 117/7 |
| 3,673,032 | 6/1972 | Komoly | 156/210 |
| 3,676,263 | 7/1972 | Tisdale | 156/462 |
| 3,679,111 | 7/1972 | Volans | 225/97 |
| 3,682,760 | 8/1972 | Fairbanks | 161/123 |
| 3,724,198 | 4/1973 | Kim | 57/140 R |
| 3,746,607 | 7/1973 | Harmon et al. | 161/109 |
| 3,839,514 | 10/1974 | Nauta | 264/1 |
| 3,849,526 | 11/1974 | Muller et al. | 264/286 |
| 3,906,073 | 9/1975 | Kim et al. | 264/147 |
| 3,965,906 | 6/1976 | Karami | 128/287 |

(List continued on next page.)

FOREIGN PATENT DOCUMENTS

WO92/04183  3/1992  European Pat. Off. ........ B32B 3/28

OTHER PUBLICATIONS

Copending commonly assigned U.S. patent application (List continued on next page.)

Primary Examiner—James J. Bell
Attorney, Agent, or Firm—Kevin C. Johnson; E. Kelly Linman

[57] ABSTRACT

An elastic, three-dimensional, fluid pervious, polymeric web is provided for use as a topsheet on an absorbent article. The web has a plurality of beam-like elements connected to one another forming apertures in the web. A plurality of the beam-like elements have permanently deformed sections which allow the web to extend when the web is subjected to tension providing an increased elasticity to the web.

15 Claims, 11 Drawing Sheets

U.S. PATENT DOCUMENTS

| | | | |
|---|---|---|---|
| 3,966,868 | 6/1976 | Hope et al. | 264/238 |
| 3,969,473 | 7/1976 | Meek | 264/90 |
| 3,969,565 | 7/1976 | Forrest | 264/284 |
| 3,994,299 | 11/1976 | Karami | 128/287 |
| 4,083,914 | 4/1978 | Schippers et al. | 264/147 |
| 4,101,358 | 7/1978 | Kim et al. | 156/167 |
| 4,101,625 | 7/1978 | Haley | 264/287 |
| 4,144,008 | 3/1979 | Schwarz | 425/66 |
| 4,147,291 | 4/1979 | Akao et al. | 229/55 |
| 4,153,664 | 5/1979 | Sabee | 264/289 |
| 4,184,902 | 1/1980 | Karami | 156/85 |
| 4,200,963 | 5/1980 | Kamfe et al. | 26/73 |
| 4,223,059 | 9/1980 | Schwarz | 428/198 |
| 4,258,848 | 3/1981 | Akao et al. | 206/524.2 |
| 4,280,978 | 7/1981 | Dannheim et al. | 264/156 |
| 4,336,638 | 6/1982 | Mercer | 26/99 |
| 4,342,314 | 8/1982 | Radel et al. | 128/287 |
| 4,374,690 | 2/1983 | Canterino et al. | 156/229 |
| 4,475,971 | 10/1984 | Canterino | 156/163 |
| 4,517,714 | 5/1985 | Sneed et al. | 28/103 |
| 4,614,632 | 9/1986 | Kezuka et al. | 264/280 |
| 4,806,300 | 2/1989 | Walton et al. | 264/288.8 |
| 5,143,679 | 9/1992 | Weber et al. | 264/288.8 |

OTHER PUBLICATIONS of Weil et al., Ser. No. 07/714,476, filed Jun. 13, 1991, entitled "Absorbent Article with Fastening System Providing Dynamic Elasticized Waistband Fit".

Copending commonly assigned U.S. patent application of Buell et al., Ser. No. 07/750,775, filed Aug. 22, 1991, entitled "Absorbent Article with Dynamic Elastic Waist Feature Having a Predisposed Resilient Flexural Hinge".

Copending commonly assigned U.S. patent application of Clear et al., Ser. No. 07/750,774, filed Aug. 8, 1991, entitled "Absorbent Article with Dynamic Elastic Waist Feature Comprising an Expansive Tummy Panel".

Copending commonly assigned U.S. patent application of Weber et al., Ser. No. 07/662,536, filed Feb. 28, 1991, entitled "Improved Method and Apparatus for Incrementally Stretching Zero Strain Stretch Laminate Web to Impact Elasticity Thereto".

Copending commonly assigned U.S. patent application of Buell et al., Ser. 07/662,537, filed Feb. 28, 1991, entitled "Improved Method and Apparatus for Incrementally Stretching Zero Strain Laminate Web in a Non-Uniform Manner to Impart a Varying Degree of Elasticity Thereto", Issuing Oct. 10, 1992 as U.S. Pat. No. 5,156,793.

POLYMERIC WEB HAVING DEFORMED SECTIONS WHICH PROVIDE A SUBSTANTIALLY INCREASED ELASTICITY TO THE WEB

FIELD OF THE INVENTION

The present invention relates to resilient, three-dimensional, fluid pervious, polymeric webs comprised of a plurality of beam-like elements connected to one another to form apertures in the web, and more particularly, to such webs wherein a plurality of the beam-like elements have deformed sections providing a substantially increased elasticity to the web.

BACKGROUND INFORMATION

It has long been known in the disposable absorbent bandage art that it is extremely desirable to construct absorptive devices such as disposable diapers, catamenial pads, sanitary napkins, incontinent articles, and the like, presenting a dry surface feel to the user to improve wearing comfort and to minimize the development of undesirable skin conditions due to prolonged exposure to moisture absorbed within the bandage.

A viable prior art solution to the aforementioned problem is an absorbent article having an apertured formed film topsheet. Apertured formed film topsheets are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Apertured formed film topsheets have enjoyed widespread commercial success on absorbent articles due to their clean and dry appearance in use when contrasted to conventional nonwoven fibrous topsheets.

Another way of improving the comfort and fit of absorbent articles is to make them stretchable such that they provide garment like characteristics. While a stretchable article has improved comfort and fit the materials used to make such articles is cost prohibitive for disposable absorbent articles. For example, in order to make the topsheet stretchable an elastomeric material is used.

Accordingly, it is an object of the present invention to provide, in a particularly preferred embodiment, a fluid pervious polymeric web having an increased elasticity.

It is another object of the present invention to provide, in a particularly preferred embodiment, an extensible article having a fluid pervious polymeric topsheet with an increased elasticity.

It is another object of the present invention to provide, in a particularly preferred embodiment, a fluid pervious polymeric web having an increased elasticity at minimal costs.

SUMMARY OF THE INVENTION

The present invention pertains, in a preferred embodiment, to an elastic, three-dimensional, fluid pervious, polymeric web having a first direction and a second direction perpendicular thereto. The web has a plurality of beam-like elements which are connected to one another to form apertures in the web. The beam-like elements have a base portion in an uppermost plane and a pair of sidewall portions depending from the base portion. A plurality of the beam-like elements have permanently deformed sections such that the base portion of the deformed section is below the uppermost plane while the web is in a substantially non-tensioned state. The base portion of the permanently deformed section is elevated towards the uppermost plane when the web is subjected to tension in the first direction allowing the web to extend in the first direction and the base portion of the permanently deformed section returns to its non-tensioned position below the uppermost plane when the tension in the web is released.

In another preferred embodiment, the present invention provides an absorbent bandage comprising a wearer-contacting topsheet and an absorbent element for absorbing bodily fluid. The topsheet comprises an elastic three-dimensional fluid pervious polymeric web having a first direction and a second direction perpendicular thereto. The web has a plurality of beam-like elements connected to one another forming apertures in the web. The beam-like elements have a base portion in an uppermost plane and a pair of sidewall portions depending from the base portion and contacting the absorbent element. A plurality of the beam-like elements have permanently deformed sections such that the base portion of the permanently deformed section is below the uppermost plane while the web is in a substantially non-tensioned state. The base portion of the deformed section is elevated towards the uppermost plane when the web is subjected to tension in the first direction allowing the web to extend in the first direction and the base portion of the permanently deformed section returns to its non-tensioned position below the uppermost plane when the tension in the web is released.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numerals identify identical elements and wherein;

DETAILED DESCRIPTION OF THE PRESENT INVENTION

As used herein, the term "absorbent article" refers to devices which absorb and contain body exudates, and, more specifically, refers to devices which are placed against or in proximity to the body of the wearer to absorb and contain the various exudates discharged from the body. The term "absorbent article" is intended to include diapers, catamenial pads, sanitary napkins, pantiliners, incontinent pads, and the like. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
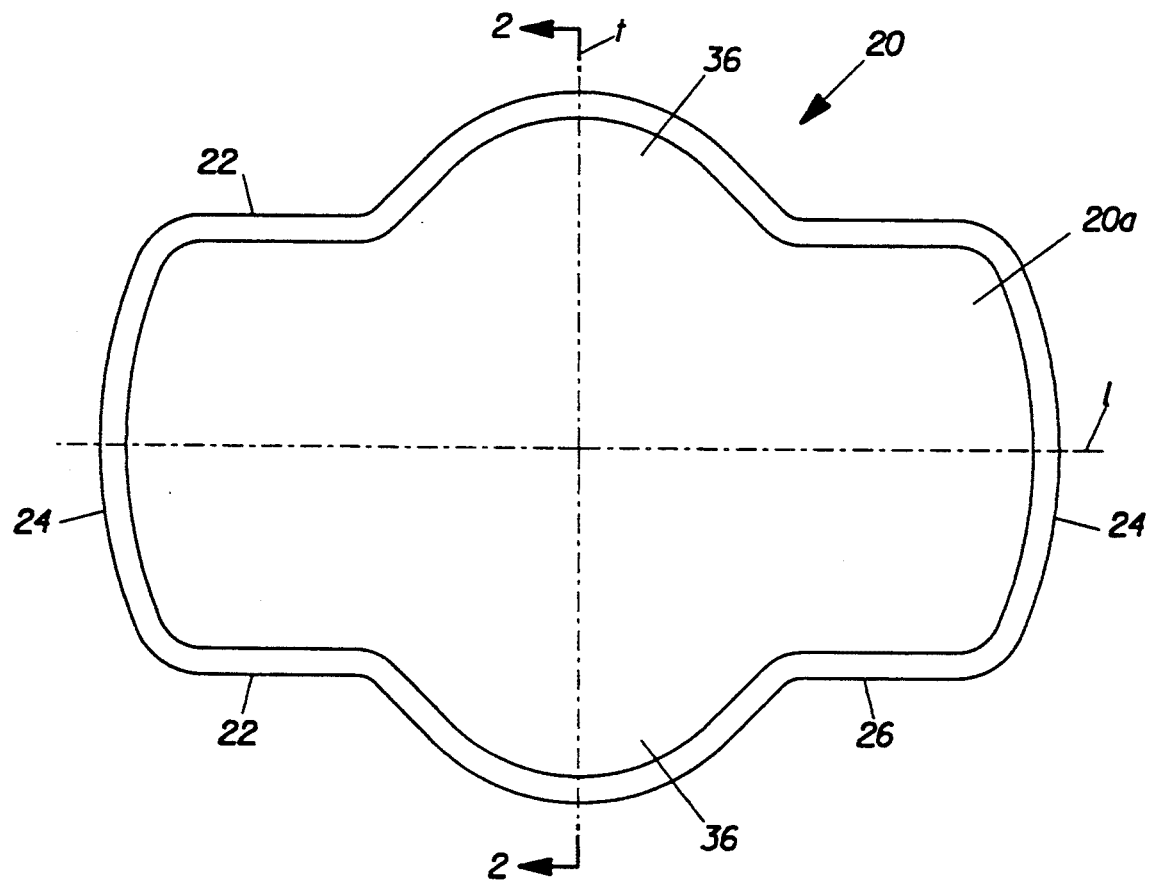
FIG. 1 is a top plan view of a preferred sanitary napkin embodiment of the present invention.

A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

The sanitary napkin 20 has two surfaces, a body-contacting surface or "body surface" 20a and a garment surface 20b. The sanitary napkin 20 is shown in FIG. 1 as viewed from its body surface 20a. The body surface 20a is intended to be worn adjacent to the body of the wearer. The garment surface 20b of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline "l" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction. FIG. 1 shows that the sanitary napkin 20 also has two spaced apart longitudinal or side edges 22 and two spaced apart transverse or end edges (or "ends") 24, which together form the periphery 26 of the sanitary napkin 20.

Figure 2:
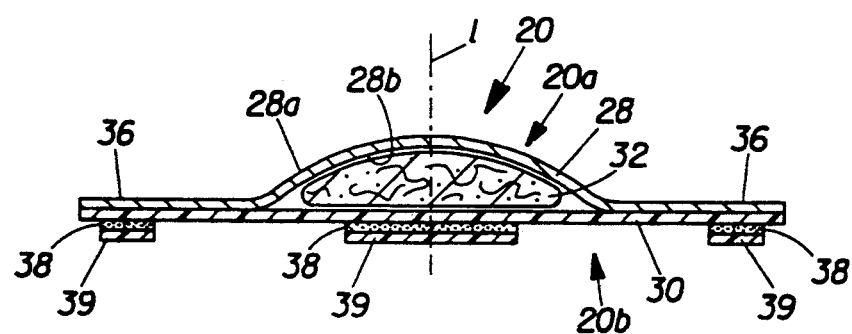
FIG. 2 is a simplified cross-sectional view of the sanitary napkin of FIG. 1 taken along section line 2—2.

The sanitary napkin 20 can be of any thickness, including relatively thick or relatively thin. The embodiment of the sanitary napkin 20 shown in FIGS. 1–2 is intended to be an example of a relatively thin sanitary napkin. It should be understood, however, when viewing these figures the number of layers of material shown cause the sanitary napkin 20 to appear much thicker then it actually is. A "thin" sanitary napkin 20 preferably has a caliper of less than about 3 millimeters. The thin sanitary napkin 20 shown should also be relatively flexible, so that it is comfortable for the wearer.

Preferably, the sanitary napkin 20 is extensible or stretchable. Examples of extensible or stretchable sanitary napkins are disclosed in U.S. patent application Ser. No. 07/915,133 filed Jul. 23, 1992 in the name of Osborn, et al. and U.S. patent application Ser. No. 07/913,204 filed Jul. 23, 1992 in the name of Osborn, et al.

FIG. 2 is a cross-sectional view of the sanitary napkin 20 taken along section line 2—2 of FIG. 1. FIG. 2 shows the individual components of the sanitary napkin 20. The sanitary napkin of the present invention generally comprises at least three primary components. These include a liquid pervious topsheet 28, a liquid impervious backsheet (or "barrier means") 30, and an absorbent core 32. The absorbent core 32 is positioned between the topsheet 28 and the backsheet 30. The sanitary napkin 20 preferably includes optional side flaps or "wings" 36 that are folded around the crotch portion of the wearer's panties. The sanitary napkin 20 shown also has an adhesive fastening means 38 for attaching the sanitary napkin 20 to the undergarment of the wearer. Removable release liners 39 cover the adhesive fastening means 38 to keep the adhesive from sticking to a surface other than the crotch portion of the undergarment prior to use.

The absorbent core 32 may be any absorbent means which is capable of absorbing or retaining liquids (e.g., menses and/or urine). As shown in FIG. 2, the absorbent core 32 has a body surface, a garment surface, side edges, and end edges. The absorbent core 32 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; chemically stiffened, modified or cross-linked cellulosic fibers; capillary channel fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core may also be varied (e.g., the absorbent core 32 may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 32 should, however, be compatible with the design loading and the intended use of the sanitary napkin 20. Further, the size and absorbent capacity of the absorbent core 32 may be varied to accommodate different uses such as incontinence pads, pantiliners, regular sanitary napkins, or overnight sanitary napkins. In addition, the absorbent core 32 may be comprised of certain materials or configurations to provide flexibility if so desired.

Exemplary absorbent structures for use as the absorbent core 32 of the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The backsheet 30 and the topsheet 28 are positioned adjacent the garment surface and the body surface, respectively, of the absorbent core 32 and are preferably joined thereto and to each other by attachment means (not shown) such as those well known in the art. For example, the backsheet 30 and/or the topsheet 28 may be secured to the absorbent core 32 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 30 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 30 prevents the exudates absorbed and contained in the absorbent core 32 from wetting articles which contact the sanitary napkin 20 such as pants, pajamas and undergarments. The backsheet 30 may thus comprise a woven or nonwoven material, polymeric films such as thermoplastic films of polyethylene or polypropylene, or composite materials such as a film-coated nonwoven material . Preferably, the backsheet 30 i s a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet 30 is preferably embossed and/or matte finished to provide a more clothlike appearance. Further, the backsheet 30 may permit vapors to escape from the absorbent core 32 (i.e., breathable) while still preventing exudates from passing through the backsheet 30.

The topsheet 28 is fluid pervious permitting liquids (e.g., menses and/or urine) to readily penetrate through its thickness and when the sanitary napkin 20 is in use, the topsheet 28 is in close proximity to the skin of the user. The topsheet 28 is compliant, soft feeling, and non-irritating to the wearer's skin.

The topsheet 28 has two sides (or faces or surfaces), including a body-facing side 28a and a garment-facing side (or core-facing side) 28b. The body-facing side 28a of the topsheet 28 generally forms at least a portion of the body-contacting surface ("body surface") 20a of the sanitary napkin 20.

Figure 3:
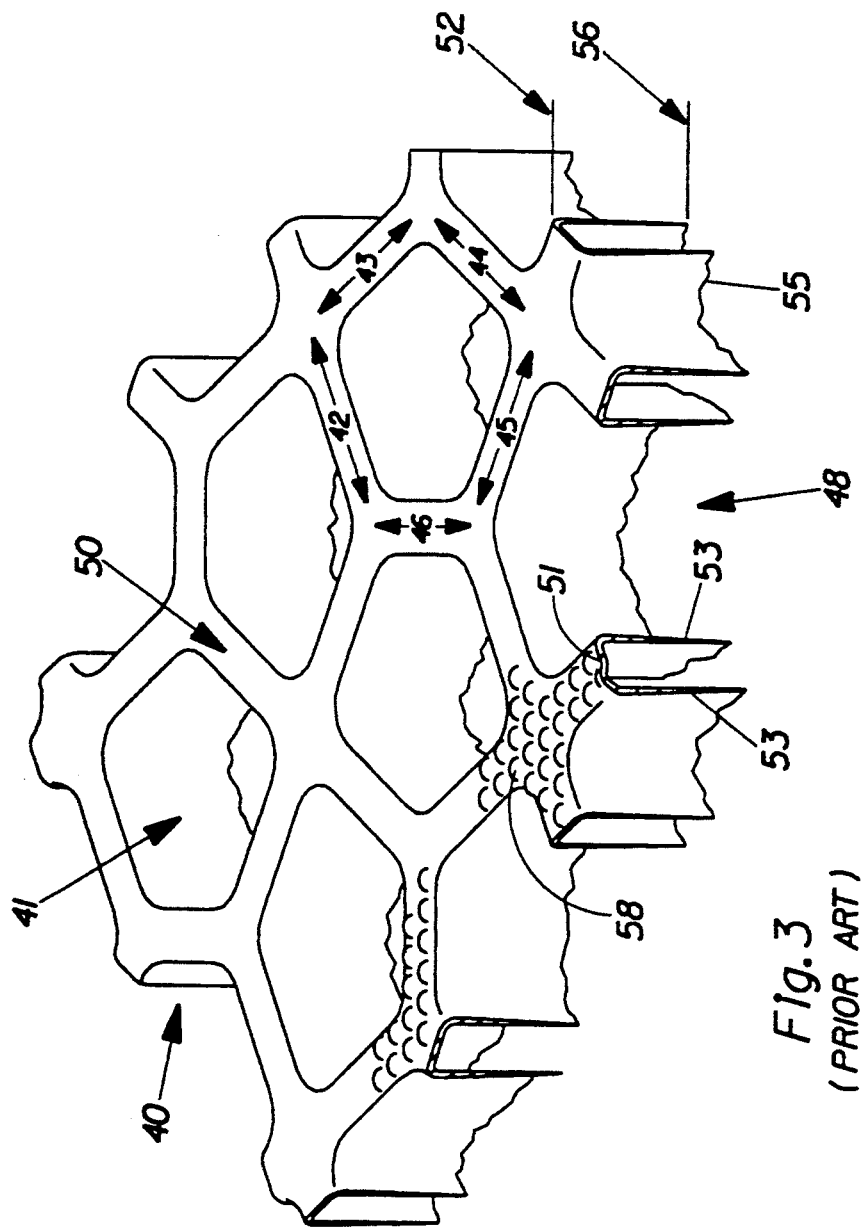
FIG. 3 is an enlarged, partially segmented, perspective illustration of a prior art plastic web of the type generally disclosed in commonly assigned U.S. Pat. No 4,342,314, said web further exhibiting a microscopic pattern of surface aberrations of the type generally disclosed in commonly assigned U.S. Pat. No. 4,463,045 on its visible surface.

FIG. 3 is an enlarged, partially segmented, perspective illustration of a prior art three-dimensional, beam-like, fluid pervious plastic web 40 which has been found highly suitable for use as a topsheet 28 for a sanitary napkin 20. The prior art web 40 is generally in accordance with the teachings of commonly assigned U.S. Pat. No. 4,342,314 issued to Radel et al. on Aug. 3, 1982 and incorporated herein by reference. The fluid pervious plastic web 40 illustrated in FIG. 3 exhibits a multiplicity of apertures, e.g., apertures 41, which are formed by a multiplicity of intersecting beam-like elements, e.g., elements 42, 43, 44, 45 and 46 interconnected to one another in the first surface 50 of the web. Each beam-like element comprises a base portion, e.g., base portion 51, located in uppermost plane 52. Each base portion has a sidewall portion, e.g., sidewall portions 53, attached to each edge thereof. The sidewall portions extend generally in the direction of the second surface 55 of the web. The intersecting sidewall portions of the beam-like elements are interconnected to one another intermediate the first and second surfaces of the web, and terminate substantially concurrently with one another in the lowermost plane 56 of the second surface 55.

In a particularly preferred embodiment, the base portions 51 of the prior art web 40 include a microscopic pattern of surface aberrations 58, generally in accordance with teachings of commonly assigned U.S. Pat. No. 4,463,045 issued to Ahr et al. on Jul. 31, 1984 and incorporated herein by reference. The microscopic pattern of surface aberrations 58 provide a substantially non-glossy visible surface when the web 40 is struck by incident light rays.

In a particularly preferred embodiment, the interconnected sidewall portions terminate substantially concurrently with one another in the lowermost plane of the second surface 55 to form apertures 48 in the second surface 55 of the web 40. The apertures formed by the interconnected sidewall portion allows for free transfer of fluids from the fist surface of the web to the second surface of the web without lateral transmission of fluid between adjacent apertures.

The prior art web 40 illustrated in FIG. 3 is more commonly referred to as a formed film. Apertured formed films are often used for topsheets on absorbent articles because they are pervious to body exudates and yet are non-absorbent and have reduced tendency to allow liquids to pass back through and rewet the wearer's skin. Thus, the surface of the formed film which is in contact with the body remains dry, thereby reducing body soiling and creating a more comfortable feel for the wearer. Examples of formed films are described in U.S. Pat. No. 3,929,135 issued to Thompson on Dec. 30, 1975; U.S. Pat. No. 4,324,246 issued to Mullane et al. on Apr. 13, 1982; U.S. Pat. No. 4,463,045 issued to Ahr et al. on Jul. 31, 1984; U.S. Pat. No. 4,629,643 issued to Curro et al. on Dec. 16, 1986; U.S. Pat. No. 4,637,819 issued to Ouellette et al. on Jan. 20, 1987; U.S. Pat. No. 4,839,216 issued to Curro et al. on Jun. 13, 1989; and U.S. Pat. No. 5,006,394 issued to Baird on Apr. 9, 1991. Each of these patents are incorporated herein by reference.

Figure 4:
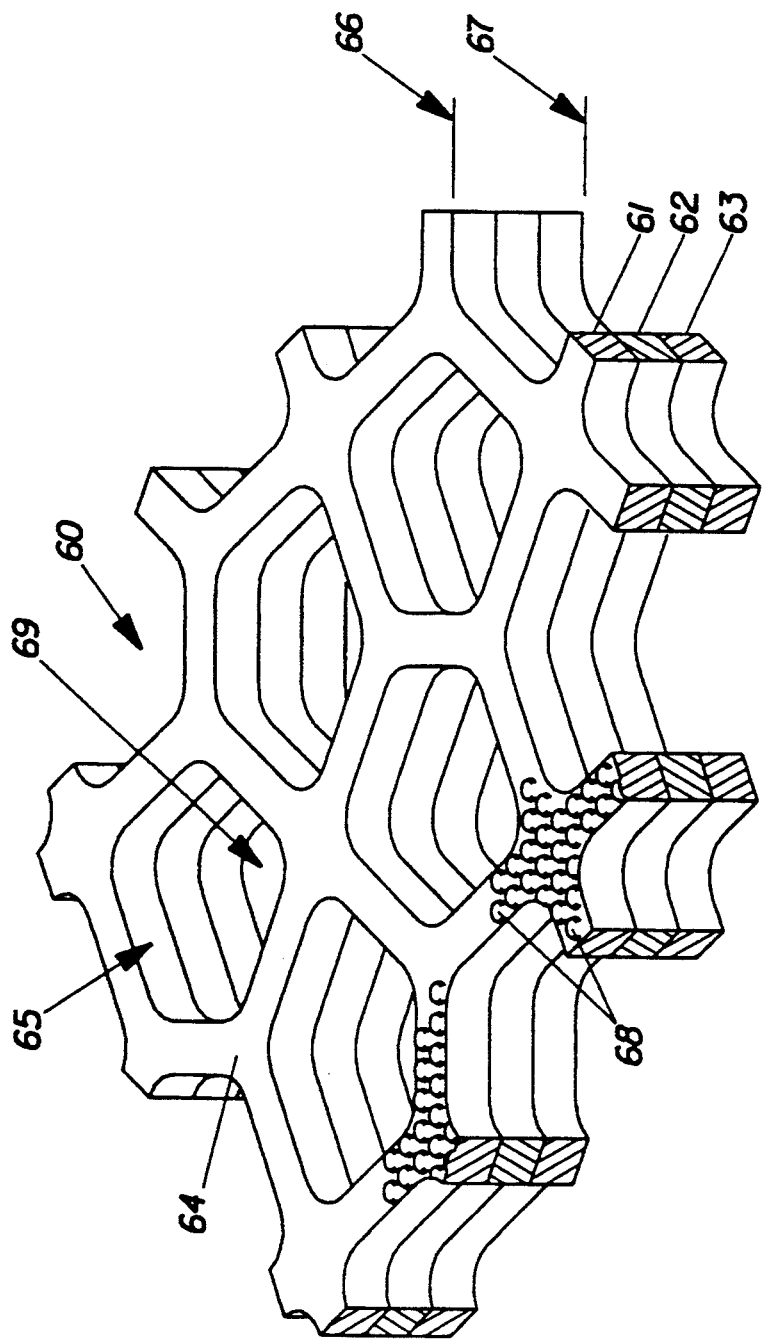
FIG. 4 is an enlarged, partially segmented perspective illustration of a photoetched laminate structure of the type used to form plastic webs of the type generally illustrated in FIG. 3.

FIG. 4 is an enlarged, partially segmented perspective illustration of a photoetched laminate structure 60 utilized to vacuum form an initially impervious, substantially planar, heated plastic film to produce a prior art, fluid pervious, beam-like web 40 of the type generally illustrated in FIG. 3. The laminate structure 60 is preferably constructed in accordance with the teaching of commonly assigned U.S. Pat. No. 4,342,314 issued to Radel et al. on Aug. 3, 1982 and incorporated herein by reference. The laminate structure 60 is comprised of individual lamina 61, 62 and 63. The aperture patterns in the individual lamina are identical to one another. A comparison of FIG. 4 with the beam-like plastic web 40 shown in FIG. 3 reveals the correspondence of aperture 41 in the uppermost plane 52 of plastic web 40 to the uppermost opening 65 in the uppermost plane 66 of the photoetched laminate structure 60. Likewise, aperture 48 in the lowermost plane 56 of plastic web 40 corresponds to the lowermost opening 69 in the lowermost plane 67 of the photoetched laminate structure 60.

The uppermost surface 64 of photoetched laminate structure 60 located in uppermost plane 66 is provided with a microscopic pattern of protuberances 68. This is preferably accomplished by applying a resist coating which corresponds to the desired microscopic pattern of surface aberrations to the top side of a planar photoetched lamina 61, and thereafter initiating a second photoetching process. The second photoetching process produces a lamina 61 having a microscopic pattern of protuberances 68 on the uppermost surface 64 of the interconnected beam-like elements defining the pentagonally shaped apertures, e.g., aperture 65. Construction of a laminate structure employing such a pattern of protuberances 68 on its uppermost layer is generally disclosed in commonly assigned U.S. Pat. No. 4,463,045 issued to Ahr et al. on Jul. 31, 1984 and is hereby incorporated herein by reference.

Figure 5:
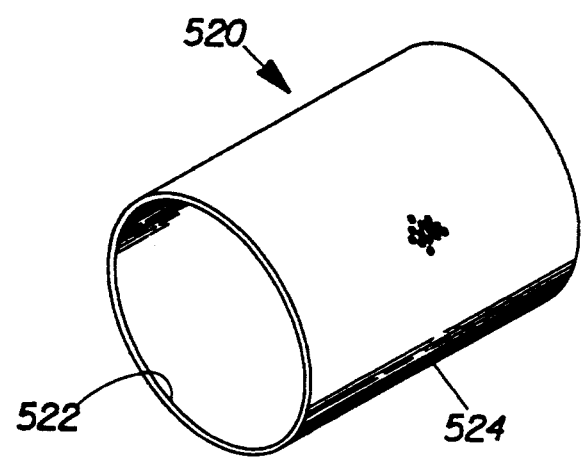
FIG. 5 is a perspective view of a tubular member formed by rolling a planar laminate structure of the type generally illustrated in FIG. 4 to the desired radius of curvature and joining the free ends to one another.

After the laminate structures have been constructed they are then rolled by conventional techniques into a tubular forming member 520, as illustrated generally in FIG. 5 and their opposing ends joined generally in accordance with the teachings of U.S. Pat. No. 4,342,314 to produce a seamless tubular forming member 520, as generally shown in FIG. 5.

Figure 6:
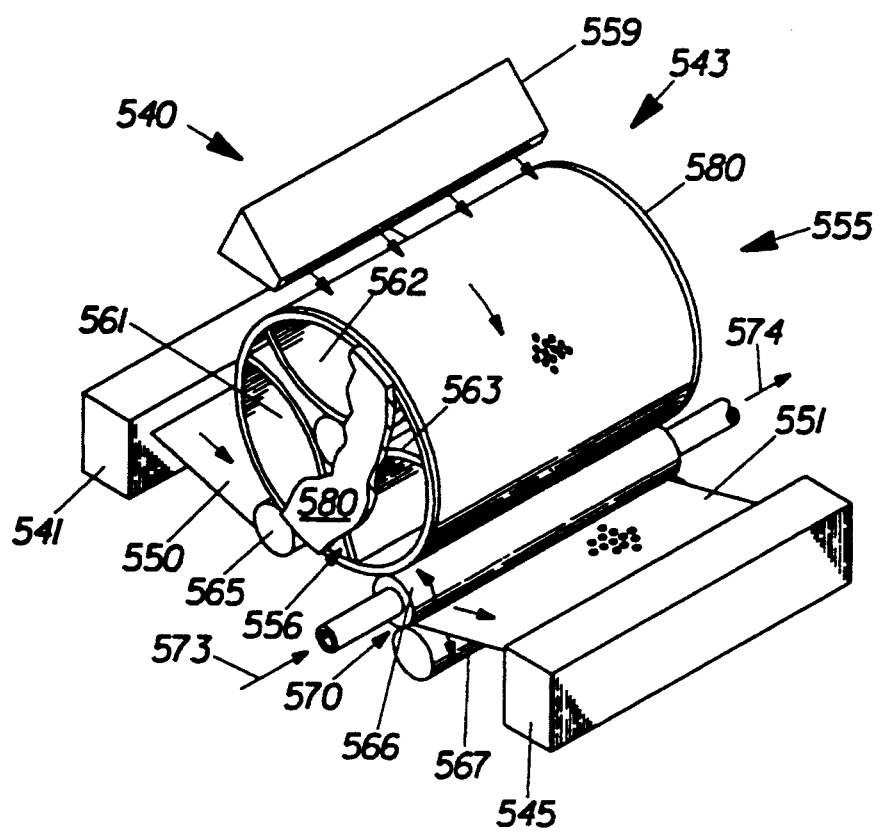
FIG. 6 is a simplified schematic illustration of a preferred method and apparatus for debossing and/or perforating a plastic film.

The outermost surface 524 of the tubular forming member 520 is utilized to form the plastic web brought in contact therewith while the innermost surface 522 of the tubular member generally does not contact the plastic web during the forming operation. The tubular member may be employed as the forming surface on debossing/perforating cylinder 555 in a process of the type generally illustrated in FIG. 6 and described in detail in U.S. Pat. No. 4,151,240 issued to Lucas et al. on Apr. 24, 1979, said patent being incorporated herein by reference. A particularly preferred apparatus 540 of the type disclosed in said patent is schematically shown in FIG. 6. It includes constant tension film supply means 541, debossing and perforating means 543, and constant tension film forwarding and winding means 545. The frame, bearing, supports and the like which must necessarily be provided with respect to the functional member of apparatus 540 are not shown or described in detail in order to simplify and more clearly depict and disclose the apparatus, it being understood that such details would be obvious to persons of ordinary skill in the art of designing plastic film converting machinery.

Briefly, apparatus 540 comprises means for continuously converting a ribbon of thermoplastic film 550 into a debossed and perforated film 551 by directing hot air jets against one surface of the film while applying vacuum adjacent the opposite surface of the film, and while maintaining sufficient control of the film 550 to substantially obviate wrinkling and/or macroscopically distending the film. Thus, as will be more fully described hereinafter, apparatus 540 comprises means for maintaining constant machine direction tension in the film both upstream and downstream of a zone where the temperature is greater than the thermoplastic temperature of the film, but in which zone there is substantially zero machine direction and cross-machine direction tension tending to macroscopically distend the film. The tension is required to control and smooth a running ribbon of thermoplastic film; the zero tension zone results from the film in the zone being at a sufficiently high temperature to enable debossing, and if desired, perforating it through the use of heat and vacuum. FIG. 6 also shows greatly enlarged scale perforations in film 551 to enable visually perceiving the nature of the difference between the imperforate film 550 and the debossed and perforated film 551 as more fully described hereinafter.

As can be seen in FIG. 6, the debossing and perforating means 543 includes a rotatably mounted debossing perforating cylinder 555 having closed ends 580, a non-rotating triplex vacuum manifold assembly 556 and hot air jet means 559. The triplex vacuum manifold assembly 556 comprises three manifolds designated 561, 562, and 563. Also shown in FIG. 6 is a freely rotatable lead-on idler roll 565, a power rotated lead-off/chill roll 566 and a soft-face (e.g., low density neoprene) roll 567 which is driven with the chill roll. Briefly, by providing means (not shown) for independently controlling the degree of vacuum in the three vacuum manifolds, a thermoplastic ribbon of film running circumferentially about a portion of the debossing-perforating cylinder 555 is sequentially subjected to a first level of vacuum by manifold 561, a second level of vacuum by manifold 562, and a third level of vacuum by manifold 563. As will be described more fully hereinafter, the vacuum applied to the film by manifold 561 enables maintaining upstream tension in the film, vacuum applied by manifold 562 enables perforating the film when hot air is directed radially inwardly against the film, and vacuum applied by manifold 563 enables cooling the film to below its thermoplastic temperature and enables establishing downstream tension therein. If desired, the film contacting surface of the debossing-perforating cylinder 555 may be preheated prior to reaching vacuum manifold 562 by means well known in the art (and therefore not shown) to facilitate better conformance of plastic films comprised of flow-resistant polymers during the debossing operation. The nip 570 intermediate chill roll 566 and the soft-face roll 567 is only nominally loaded because high pressure would iron-out the three-dimensional debossments which are formed in the film in the aforementioned manner. However, even nominal pressure in nip 570 helps the vacuum applied by manifold 563 to isolate downstream tension (i.e., roll winding tension) from the debossing-perforating portion of the debossing-perforating cylinder 555, and enables the nip 570 to peel the debossed and perforated film from the debossing-perforating cylinder 555. Moreover, while vacuum drawn ambient air passing through the film into manifold 563 will normally cool the film to below its thermoplastic temperature, the passage of coolant through the chill roll as indicated by arrows 563, 574 in FIG. 6 will enable the apparatus to handle thicker films or be operated at higher speeds.

To summarize, the first vacuum manifold 561, and the third vacuum manifold 563 located within the debossing-perforating cylinder 555 enable maintaining substantially constant upstream and downstream tension respectively in a running ribbon of film while the intermediate portion of the film adjacent the second vacuum manifold 562 within the debossing-perforating cylinder 555 is subjected to tension vitiating heat and vacuum to effect debossing and perforating of the film.

Referring again to FIG. 6, the constant tension film supply means 541 and the constant tension film forwarding and winding means 545 may, if desired, be substantially identical to and function substantially identically to the corresponding portions of the apparatus shown and described in U.S. Pat. No. 3,674,221 issued to Riemersma on Jul. 4, 1972 and which is hereby incorporated herein by reference. The debossing and perforating means 543 comprises the rotatably mounted debossing-perforating cylinder 555, means (not shown) for rotating the cylinder 555 at a controlled peripheral velocity, the non-rotating triplex vacuum manifold assembly 556 inside the debossing-perforating cylinder 555, means (not shown) for applying controlled levels of vacuum inside the three vacuum manifolds 561, 562 and 563 comprising the triplex manifold assembly 556, and hot air jet means 559.

The debossing-perforating cylinder 555 may be constructed by generally following the teachings of U.S. Pat. No. 4,151,240 issued to Lucas et al. on Apr. 24, 1979 and incorporated herein by reference, but substituting a tubular laminate forming surface of the present invention for the perforated tubular forming surface disclosed therein.

While a preferred application of the disclosed photoetched laminate structure is in a vacuum film forming operation as generally outlined in the aforementioned patent application of Lucas et al., it is anticipated that photoetched laminate forming structures could be employed with equal facility to directly form a three-dimensional plastic structure. Such a procedure would involve applying a heated fluid plastic material, typically a thermoplastic resin, directly to the forming surface applying a sufficiently great pneumatic differential pressure to the heated fluid plastic material to cause said material to conform to the image of the perforate laminate forming surface, allowing the fluid material to solidify, and thereafter removing the three-dimensional plastic structure from the forming surface. It is further anticipated that the present technology could, if desired, be incorporated in suitably reinforced film embossing rolls and the like, provided only that the embossing pressures to which the rolls will ultimately be subject are not so great as to destroy the particular three-dimensional pattern exhibited by the laminate embossing surface. A resilient back-up roll could, if desired, be utilized in such an embossing operation to avoid damaging the laminate embossing surface. It is even further anticipated that laminate forming surfaces of the present invention may find utility in applications other than plastic film forming.

Another preferred method for converting a ribbon of thermoplastic film into a three-dimensional structure is by applying a high pressure fluid against one surface of the film while jet comprised of water on the like applying a vacuum adjacent the opposite surface of the film. Such methods are described in greater detail in U.S. Pat. Nos. 4,609,518 issued to Curro et al. on Sep. 2, 1986; 4,629,643 issued to Curro et al. on Dec. 16, 1986; 4,637,819 issued to Ouellette et al. on Jan. 20, 1987; 4,695,422 issued to Curro et al. on Sep. 22, 1987; and 4,839,216 issued to Curro et al. on Jun. 13, 1989; each of said patents being incorporated herein by reference.

Figure 7:
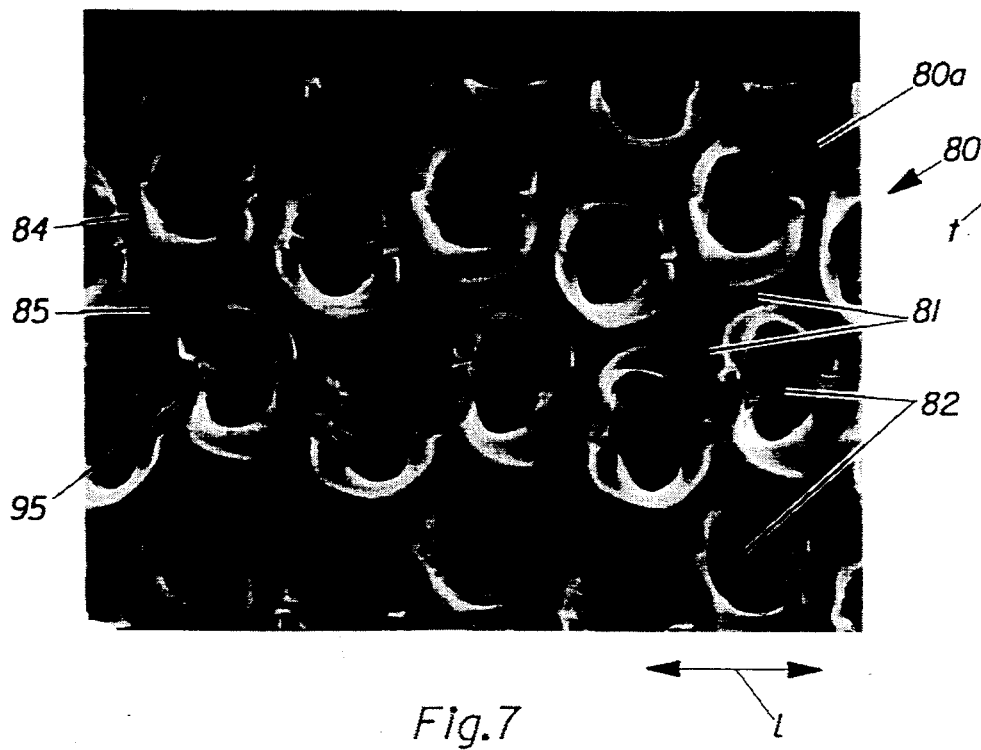
FIG. 7 is a plan view photograph enlarged approximately 20 times of a preferred web of the present invention as viewed from the wearer or body contacting surface.
Figure 8:
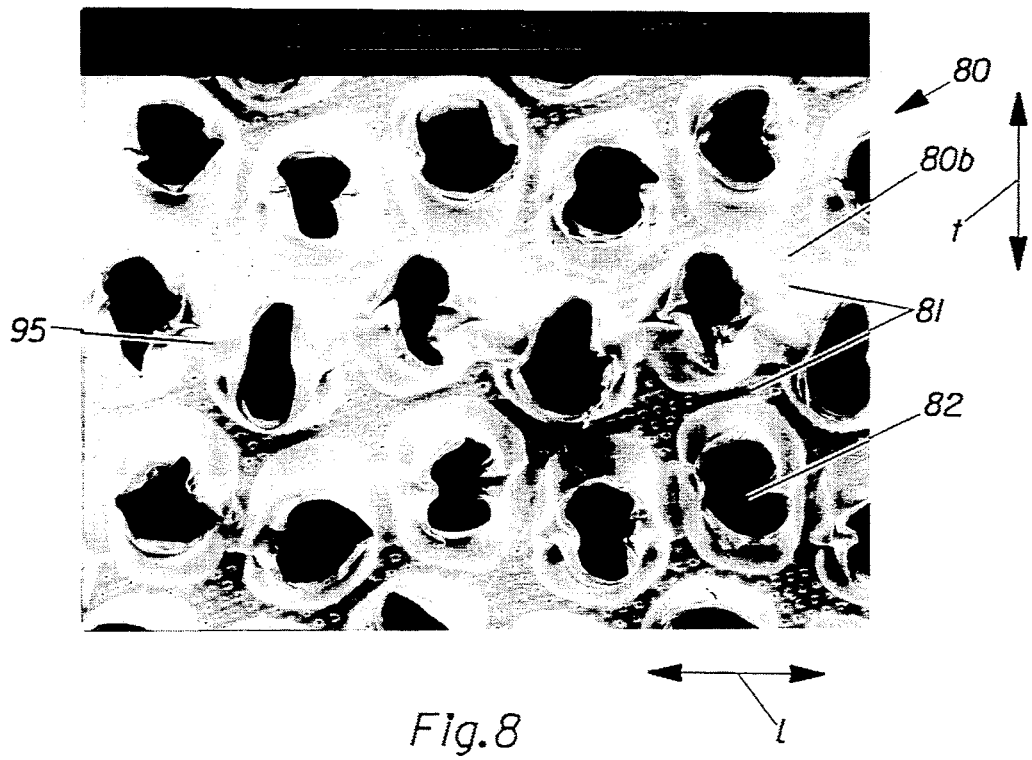
FIG. 8 is a plan view photograph enlarged approximately 20 times of the web of FIG. 7 as viewed from the garment facing or pad contacting surface.

In FIGS. 7 and 8 is shown a plan view photograph enlarged approximately 20 times actual size of a preferred embodiment of a three-dimensional, fluid-pervious plastic web 80 of the present invention. The web 80 is particularly well suited for use as a topsheet 28 on a sanitary napkin 20 of the type generally illustrated in FIGS. 1 and 2. FIG. 7 is a plan view of the wearer or body contacting surface 80a of the web 80, while FIG. 8 is a plan view of the garment facing or pad contacting surface 80b of the web 80. As can be seen in FIGS. 7 and 8, the web 80 is comprised of a plurality of beam-like elements 81 interconnected to one another to form apertures 82 in the web. As used herein the term "beam-like" is used to connote a three-dimensional structure which separates adjacent apertures in a three-dimensional formed film. A plurality of the beam-like elements 81 have permanently deformed sections 95. The permanently deformed sections 95 of the beam-like elements 81 are sections which have been elongated or incrementally stretched substantially in a particular direction, preferably the transverse direction. The transverse direction "t" is that direction which is perpendicular to the longitudinal "l" or machine direction, as will be described in detail below. The permanently deformed sections 95 of the beam-like elements 81 exhibit a somewhat saddle-shaped configuration.

Figure 9:
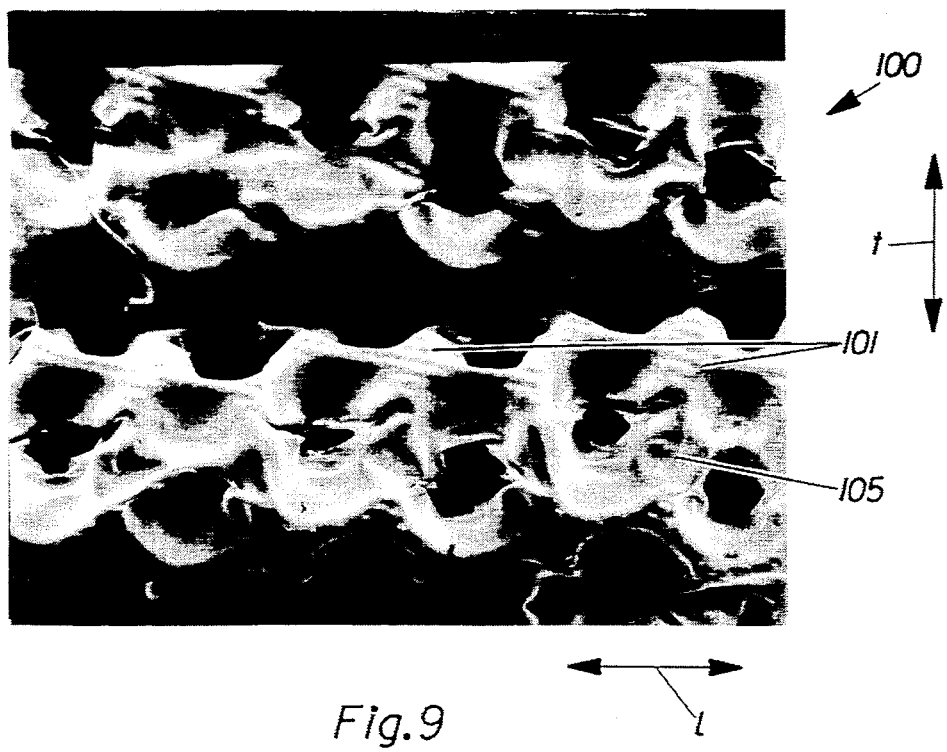
FIG. 9 is a plan view photograph enlarged approximately 20 times of another web of the present invention in a substantially non-tensioned state as viewed from the wearer or body contacting surface.
Figure 10:
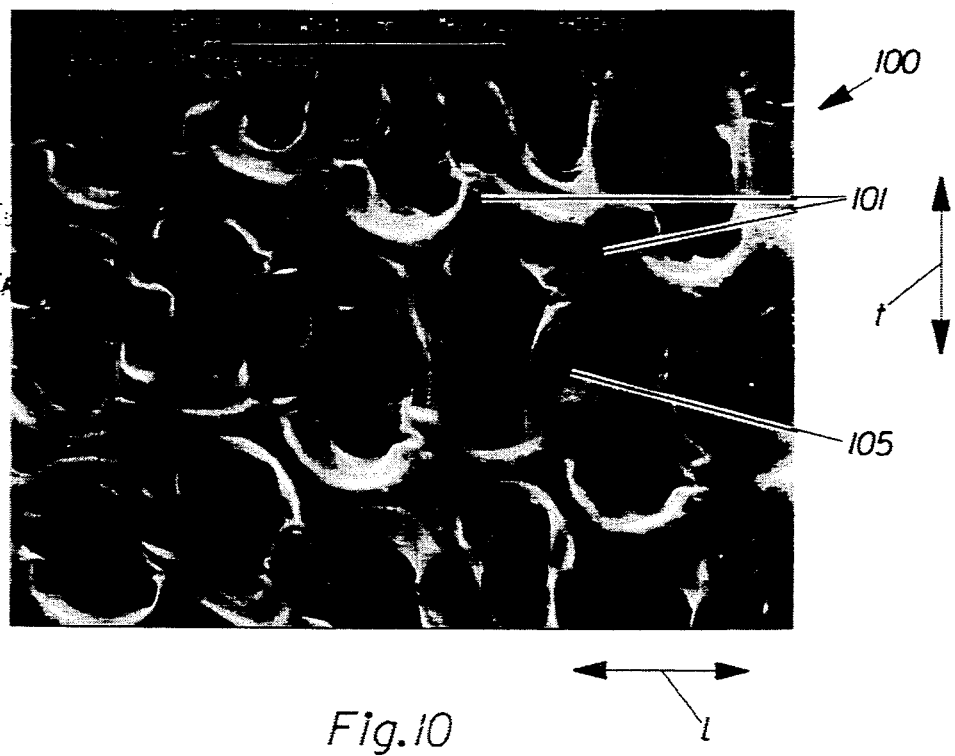
FIG. 10 is a plan view photograph enlarged approximately 20 times of the web of FIG. 9 in a substantially tensioned state as viewed from the wearer or body contacting surface.

Referring now to FIG. 9, it can be seen that the permanently deformed sections 105 of the beam-like elements 101 of the web 100 are deformed to a greater extent than the permanently deformed sections 95 of the beam-like elements 81 of the web 80 of FIGS. 7 and 8. Common to both webs 80 and 100 is that the base portions of the permanently deformed sections of the beam-like elements reside below the uppermost plane of the web while the web is in a substantially non-tensioned or relaxed state. However, when the webs are subjected to tension in the transverse direction, the base portion of the permanently deformed sections of the beam-like elements are elevated toward the uppermost plane as depicted in FIG. 10. The elevation of the permanently deformed section towards the uppermost plane of the web while the web is subjected to tension in the transverse direction allows the web to extend in the transverse direction. Upon release of the tension the permanently deformed sections of the beam-like elements return or contract to their non-tensioned or relaxed state, as shown in FIG. 9, thus providing a substantially increased elasticity to the web in the transverse direction as compared to an identical web not having beam-like elements with permanently deformed sections.

Stated succinctly, the permanently deformed sections of the beam-like elements behave as springs. As used herein, the term "spring" means an elastic body or device that recovers its original shape when released after being distorted. When subjected to tension in the transverse direction, the permanently deformed sections of the beam-like elements are extended or distorted in the direction of applied tension and return to their original shape after removal of the applied tension. Thus, the permanently deformed sections of the beam-like elements provide a substantially increased elasticity to the web.

Figure 12:
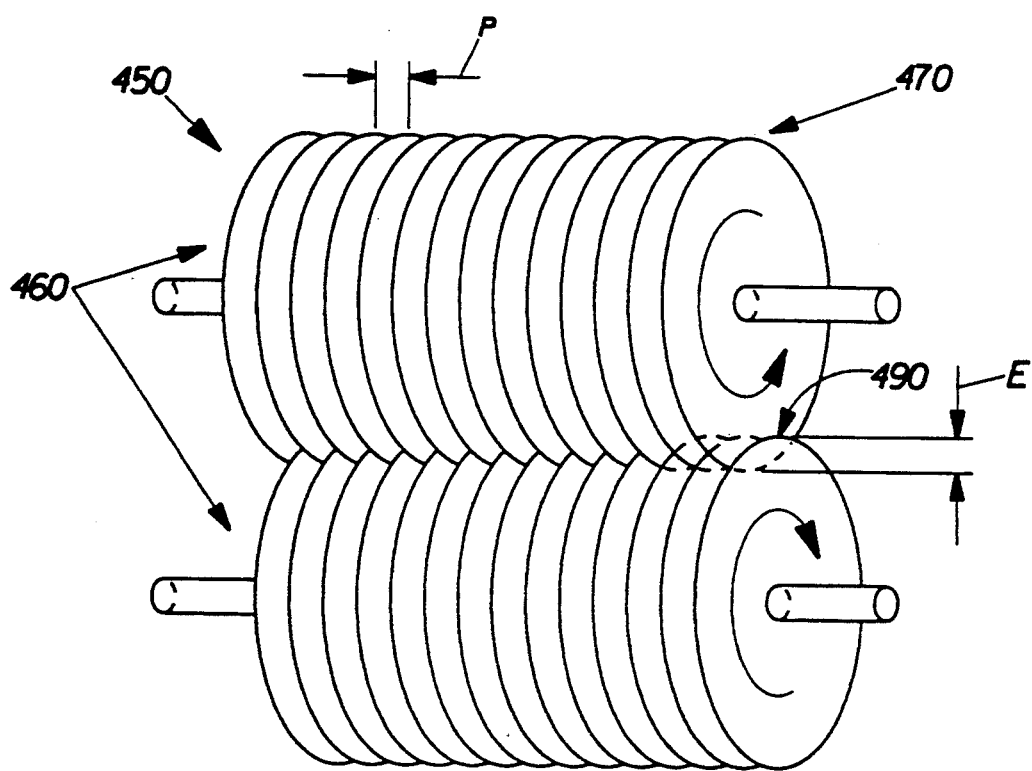
FIG. 12 is a schematic illustration of a ring-rolling apparatus such as the one used to ring-roll the three-dimensional, fluid pervious, apertured webs of the present invention.

The prior art web of FIG. 3 is substantially inelastic. However, by changing or altering its geometry the prior art web can be made to be substantially elastic. A three-dimensional, fluid pervious, polyolefin apertured web made according to the aforementioned process is longitudinally passed through rolls 460 of ring-rolling apparatus 450 illustrated in FIG. 12 to make the web of the present invention. Rolls 460 consist of teeth 470 which are separated by a uniform distance, p, more commonly known as pitch. The teeth 470 of each roll 460 are offset by a distance P/2 from each other. The distance between the outer circumferences 490 of the rolls 460 can be varied by an intermeshing distance, E, more commonly known as the engagement.

Ring-rolling of the prior art web 40 incrementally stretches and thereby plastically deforms a plurality of the beam-like elements 81 in the transverse direction. The stretching of the beam-like elements occurs incrementally across the width of the web (transverse direction) as the film is constrained at the tips of the teeth 470 and is stretched an amount that is proportional to the pitch and the engagement. As the engagement depth of the rolls 460 is increased, the incremental stretching and the plastic deformation of the beam-like elements 81 is increased. FIGS. 7 and 8 depict an elastic, three-dimensional, apertured web 80, which has been ring-rolled at an engagement of 0.075 inches and at a pitch of 0.100 inches. FIGS. 9 and 10 depict an elastic three-dimensional apertured web 100, which has been ring-rolled at an engagement of 0.150 inches and at a pitch of 0.100 inches.

A particularly preferred three-dimensional, fluid pervious apertured web of the present invention is made from low density polyethylene (LDPE) film available from Tredegar Film Products, of Terre Haute, Ind., under the designation (X-5654) and is formed by the aforementioned process, more specifically described in U.S. Pat. Nos, 4,342,314 and 4,463,045. The web, which is ten inches wide and of variable length is passed in the machine or longitudinal direction through a ring-rolling apparatus operated via a manual hand crank. The diameter of each aperture of the web is approximately 0.035 inch and the width of each beam-like element is approximately 0.007 inch. Several webs were ring-rolled at a pitch of 0.100 inch at engagements of 0.050, 0.075, 0.100, 0.125, 0.140 and 0.150 inches.

Figure 13:
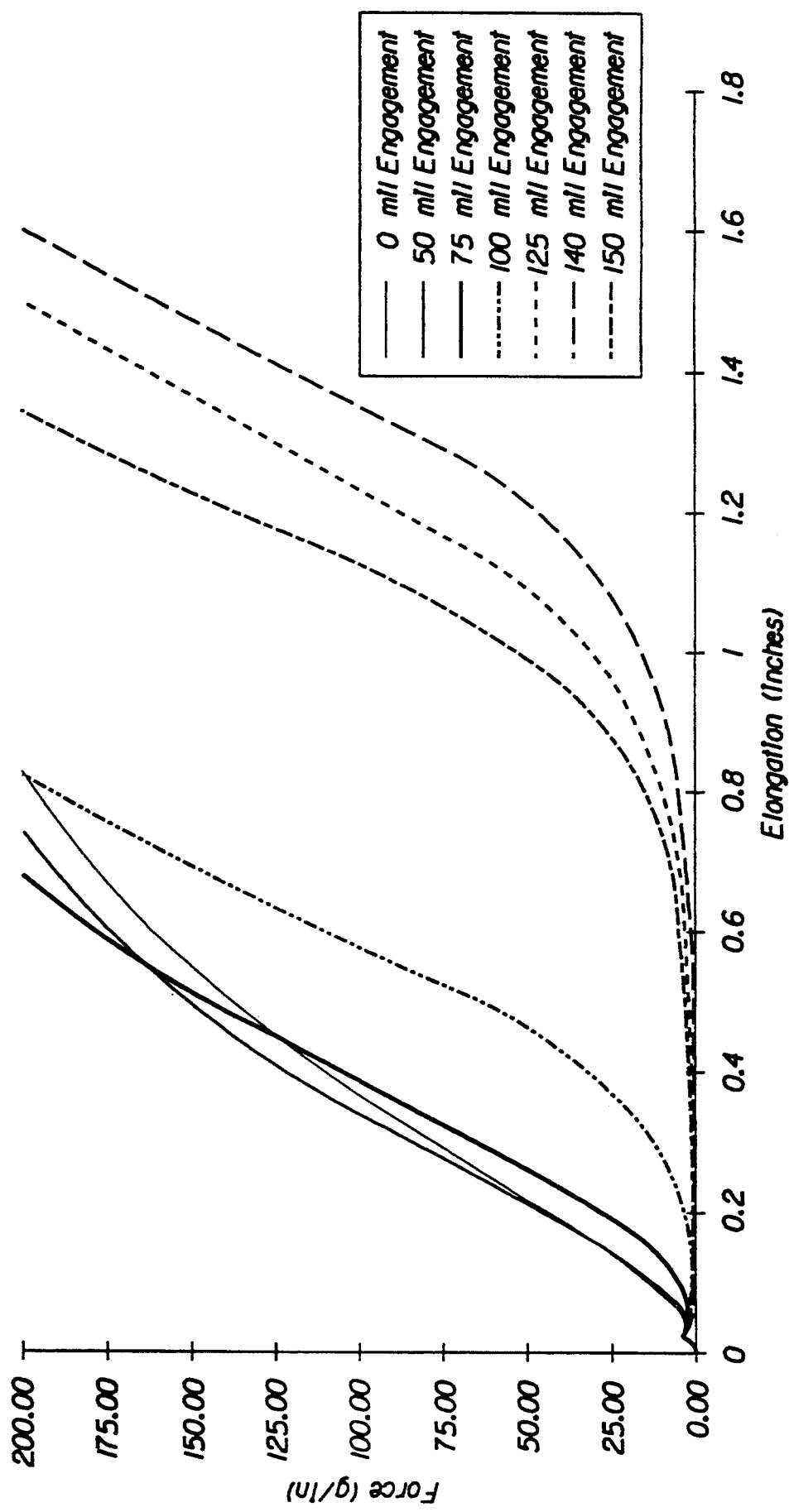
FIG. 13 is a force-elongation graph of data from a series of tensile tests conducted on web samples which were ring-rolled on 0.100 inch pitch rollers to engagement depths of 0.050, 0.075, 0.100, 0.125, 0.140, and 0.150 inches.
Figure 14:
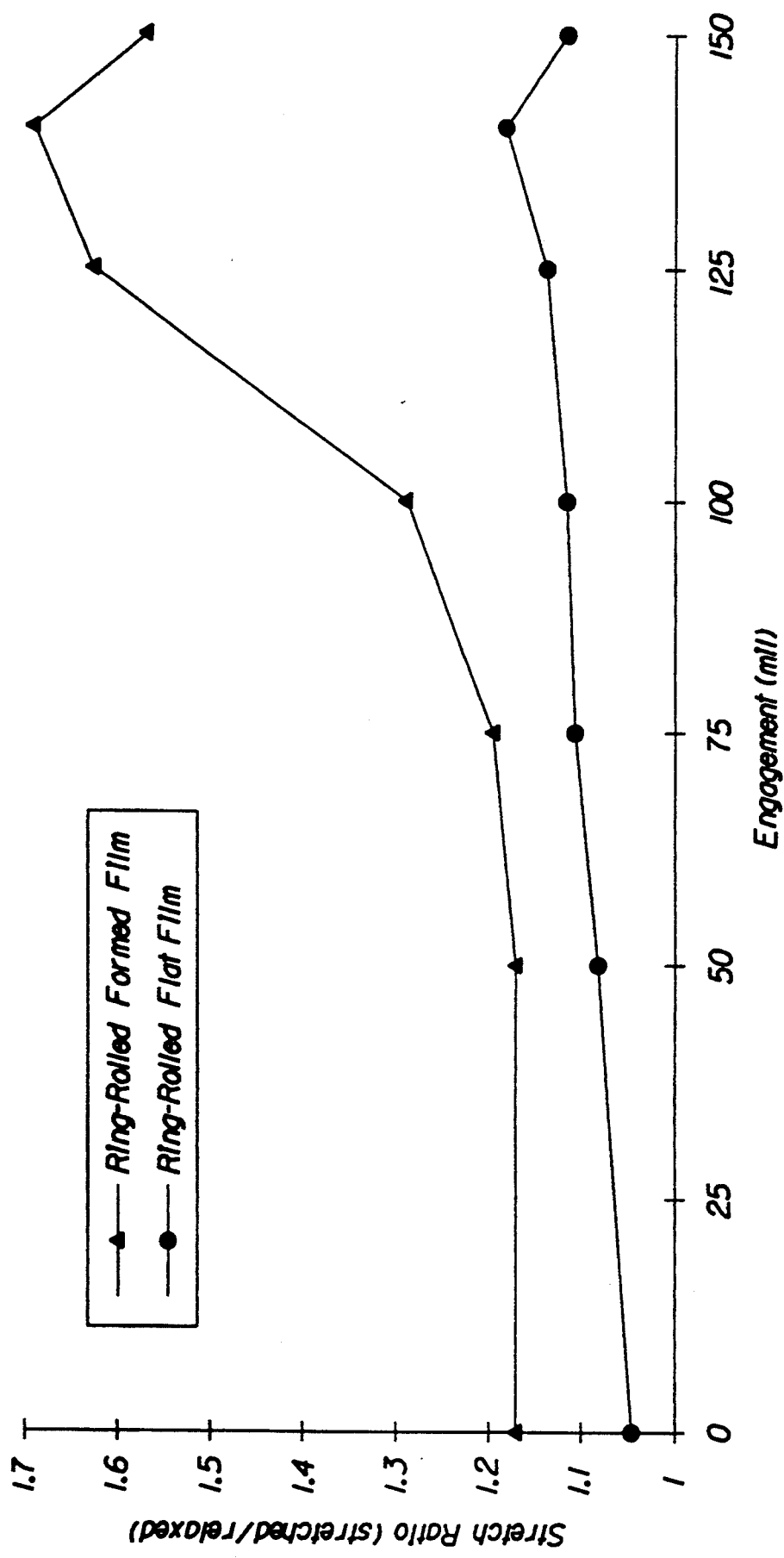
FIG. 14 is a graph of the stretch ratio versus engagement depth for the various webs.

The degree of stretch imparted to the web is experimentally determined by conducting tensile tests on an Instron Model 1125 test stand. The samples for testing are cut from the three-dimensionally apertured ring-rolled webs in 3 inch by 1 inch strips, the 3 inch dimension being in the transverse direction of the web. These samples are mounted into hydraulic grips on the Instron where the distance between the grips (known as the gage length) is two inches. Each sample is pulled at a rate of 5.0 inches per minute until it breaks. The data is plotted using Sintech's Test Works software on an IBM 386 personal computer. A graph of the force versus elongation behavior of several samples is shown in FIG. 13. The low force elastic behavior of the ring-rolled web is quantified by the stretch ratio of a web ring-rolled at a given engagement depth. The stretch ratio is defined as the length of the film at its maximum extension divided by the original gage length of the web. The maximum extension is determined by the first drawing an isoline at 100 grams on the force-elongation graph and then drawing a tangent to each curve above the 100 gram line. A force of 100 grams was selected because forces greater than 100 grams may cause increased plastic deformation of the beam-like elements of the web. The point at which these two lines intersect is called the maximum extension. This quantity is added to the original gage length to get the final length of the sample, and this sum is divided by the original gage length of the sample as shown in the following equation;

$$\text{Stretch Ratio} = \frac{L_o + x}{L_o} = \frac{L_f}{L_o}$$

where $L_o$ is the original gage length of the sample, x is the amount of elongation at maximum extension, and $L_f$ is the final length of the sample. The calculated stretch ratio for each engagement depth is plotted on a graph of stretch ratio as a function of engagement depth, see FIG. 14. This enables one to predetermine the degree of stretch obtained in the ring-rolled web by varying the engagement depth. FIG. 14 also includes a plot of the stretch ratio versus engagement depth for a ring-rolled unapertured web of the same composition as the ring-rolled apertured web. This plot was obtained in the same manner as that of the ring-rolled, three-dimensional, apertured web. Stretch ratio versus engagement depth plots of ring-rolled two-dimensionally apertured webs and lightly to highly embossed webs substantially follow the behavior of the ring-rolled unapertured web. This indicates that the low force elastic behavior described herein holds for any variety of three-dimensional, apertured webs which have been ring-rolled and does not hold for unapertured films or for two dimensional apertured films which have been ring-rolled.

Figure 11A:
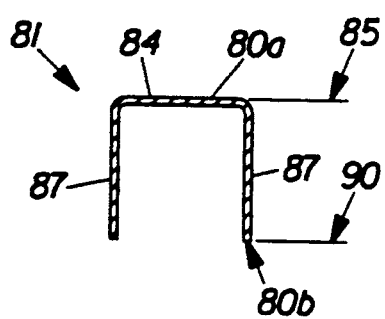
FIGS. 11A–11D are enlarged, cross-sectional illustrations of various preferred beam-like elements of the present invention.

The overall shape of the beam-like elements is non-critical provided the structure is three-dimensional. FIGS. 11A–11D are cross-sectional illustration of various beam-like geometries. FIG. 11A is a cross-sectional illustration of a preferred beam-like element 81 of the present invention. Beam-like element 81 has a base portion 84 located in an uppermost plane 85 of the first or wearer contacting surface 80a. As used herein the term "base portion" is used to connote that portion of the beam-like element 81 which contacts the wearer's skin when the absorbent article is used. A pair of sidewall portions 87 depend from the base portion 84 and extend generally in the direction of the second surface 80b, located in lowermost plane 90.

Figure 11B:
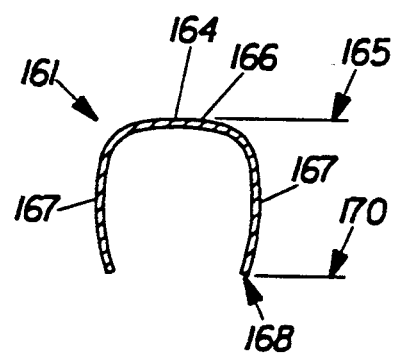

FIG. 11B is cross-sectional illustration of an alternative beam-like element 161 of the present invention. As can be seen in FIG. 11B, the beam-like element 161 comprises a base portion 164 in the uppermost plane 165 of the first or wearer contacting surface 166. A pair of sidewall portions 167 depend from the base portion 164 and extend generally in the direction of the second surface 168, located in lowermost plane 170.

Figure 11C:
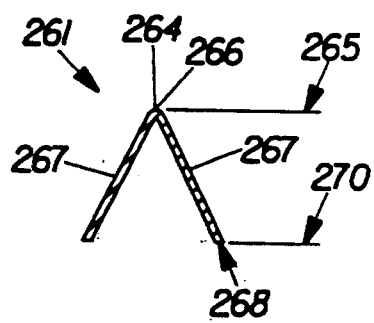

FIG. 11C is cross-sectional illustration of an alternative beam-like element 261 of the present invention. As can be seen in FIG. 11C, the beam-like element 261 comprises a base portion 264 in the uppermost plane 265 of the first or wearer contacting surface 266. A pair of sidewall portions 267 depend from the base portion 264 and extend generally in the direction of the second surface 268, located in lowermost plane 270.

Figure 11D:
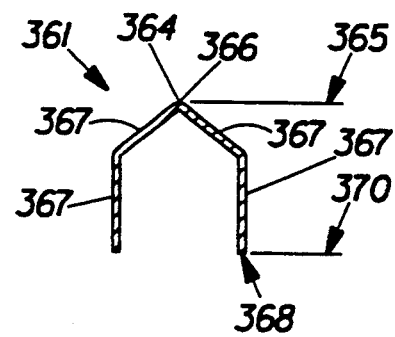

FIG. 11D is cross-sectional illustration of an alternative beam-like element 361 of the present invention. As can be seen in FIG. 11D, the beam-like element 361 comprises a base portion 364 in the uppermost plane 365 of the first or wearer contacting surface 366. A pair of sidewall portions 367 depend from the base portion 364 and extend generally in the direction of the second surface 368 located, in lowermost plane 370.

In addition to having various cross-sectional geometries, the cross-section of the beam-like elements may be either substantially uniform or non-uniform along this length. An example of a beam-like element having a substantially uniform cross-section along its length is illustrated in U.S. Pat. No. 4,342,314 issued to Radel et al. An example of a beam-like element having a non-uniform cross-section along its length is illustrated in U.S. Pat. No. 3,929,135 issued to Thompson et al. Said patents being incorporated herein by reference.

While the present invention has been described as subjecting an entire web to ring-rolling in one particular direction, the present invention is in no way limited to such application. The present invention may also be practiced by subjecting only predetermined discrete portions of the web to ring-rolling. For example, it may be desirable to ring-roll a discrete portion of the web which when used as a topsheet on an absorbent article corresponds to the central portion of the absorbent article. The present invention may also be practiced by ring-rolling the web in more than one direction to impart an increased elasticity to the web in more than one direction.

In addition to providing a substantially increased elasticity to the web, ring-rolling of prior art web also changes other resultant properties of the web. The drape, stretched open-area, and ultimate tensile strength of the ring-rolled web typically increase. Furthermore, the gloss and effective stretched basis weight of the ring-rolled web are typically decreased.

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al. Alternatively, the body surface of the topsheet can be made hydrophilic by treating it with a surfactant such as is described in the above referenced U.S. Pat. No. 4,950,254 issued to Osborn.

In use, the sanitary napkin 20 can be held in place by any support means or attachment means well-known for such purposes. Preferably, the sanitary napkin 20 is placed in the user's undergarment or panty and secured thereto by a fastener such as an adhesive 38, shown in FIG. 2. The adhesive 38 provides a means for securing the sanitary napkin 20 in the crotch portion of the panty. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the sanitary napkin is placed in use, the pressure-sensitive adhesive is typically covered with a removable release liner 39 in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/O and BL30MG-A Silox 4P/O both of which are manufactured by the Akrosil Corporation of Menasha, Wis. The sanitary napkin 20 of the present invention is used by removing the release liner 39 and thereafter placing the sanitary napkin in a panty so that the adhesive contacts the panty. The adhesive 38 maintains the sanitary napkin 20 in its position within the panty during use.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An elastic, three-dimensional, fluid pervious, polymeric web having a first direction and a second direction perpendicular thereto, said web comprising: a plurality of three-dimensional, beam-like elements having a base portion in an uppermost plane and a pair of sidewall portions depending from said base portion connected to one another forming apertures in said web, a plurality of said three-dimensional, beam-like elements having permanently deformed sections such that said base portion of said permanently deformed section is below said uppermost plane while said web is in a substantially non-tensioned state, said base portion of said permanently deformed section being elevated towards said uppermost plane when said web is subjected to tension in the first direction allowing said web to extend in the first direction and said base portion of said permanently deformed section returning to its non-tensioned position below said uppermost plane when the tension in said web is released.

2. The elastic, three-dimensional web of claim 1, wherein at least a portion of said three-dimensional, beam-like elements are substantially straight along a portion of their length.

3. The elastic, three-dimensional web of claim 1, wherein at least a portion of said three-dimensional, beam-like elements are substantially straight along their entire length.

4. The elastic, three-dimensional web of claim 1, wherein said apertures are of non-uniform cross-section along their length.

5. The elastic three-dimensional web of claim 1, wherein said apertures are of decreasing cross-section in the direction of said second surface, thereby promoting rapid transmission fluids deposited on said apertures in said first surface to the corresponding apertures in said second surface without lateral transmission of said fluids between adjacent apertures.

6. The elastic, three-dimensional web of claim 1, wherein a plurality of said three-dimensional, beam-like elements having permanently deformed sections are located in predetermined discrete portions of said web.

7. The elastic, three-dimensional web of claim 1, wherein said base portion of said permanently deformed section is elevated towards said uppermost plane when said web is subjected to tension in the second direction allowing said web to extend in the second direction and said base position of said permanently deformed section returning to its non-tensioned portion below said uppermost plane when the tension in said web is released.

8. An absorbent article comprising a wearer-contacting topsheet and an absorbent element for absorbing bodily fluids, said topsheet comprising an elastic, three-dimensional, fluid pervious, polymeric web having a first direction and a second direction perpendicular thereto, said web comprising: a plurality of three-dimensional beam-like elements having a base portion in an uppermost plane and a pair of sidewall portions depending from said base portion connected to one another forming apertures in said web, a plurality of said three-dimensional, beam-like elements having permanently deformed sections such that said base portion of said permanently deformed section is below said uppermost plane while said web is in a substantially non-tensioned state, said base portion of said permanently deformed section being elevated towards said uppermost plane when said web is subjected to tension in the first direction allowing said web to extend in the first direction and said base portion of said permanently deformed section returning to its non-tensioned position below said uppermost plane when the tension in said web is released.

9. The absorbent article of claim 8, including a backsheet resistant to the passage of aqueous fluid therethrough secured in superposed relation to said absorbent article adjacent the surface of said absorbent element opposite said topsheet.

10. The structure of claim 9, wherein said absorbent article comprises a catamenial appliance.

11. The structure of claim 10, wherein said catamenial appliance is extensible or stretchable.

12. The structure of claim 9, wherein said absorbent article comprises a disposable diaper.

13. The structure of claim 9, wherein said absorbent article is extensible or stretchable.

14. The structure of claim 9, wherein a plurality of said three-dimensional beam-like elements having permanently deformed sections are located in predetermined discrete portions of said web.

15. The structure of claim 9, wherein said base portion of said permanently deformed section is elevated towards said uppermost plane when said web is subjected to tension in the second direction allowing said web to extend in the second direction and said base position of said permanently deformed section returning to its non-tensioned portion below said uppermost plane when the tension in said web is released.

* * * * *